(12) United States Patent
Wolleschensky

(10) Patent No.: US 6,521,899 B1
(45) Date of Patent: Feb. 18, 2003

(54) ARRANGEMENT FOR THE ADJUSTMENT OF LASER POWER AND/OR PULSE LENGTH OF A SHORT PULSE LASER IN A MICROSCOPE

(75) Inventor: Ralf Wolleschensky, Schoeten (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/559,196

(22) Filed: Apr. 27, 2000

(30) Foreign Application Priority Data

Apr. 27, 1999 (DE) .......................... 199 19 091

(51) Int. Cl.⁷ .......................... G02B 21/00; G01N 21/64
(52) U.S. Cl. .................. 250/458.1; 250/459.1
(58) Field of Search .......................... 250/458.1, 459.1, 250/461.1, 462.1

(56) References Cited

U.S. PATENT DOCUMENTS 5,034,613 A * 7/1991 Denk et al. .............. 250/458.1
6,166,385 A * 12/2000 Webb et al. .............. 250/458.1
6,167,173 A   12/2000 Guenter et al.
6,169,289 B1 * 1/2001 White et al. .............. 250/458.1

FOREIGN PATENT DOCUMENTS

DE   197 02 753 A1   7/1998
DE   695 13 517 T2   6/2000

* cited by examiner

Primary Examiner—Constantine Hannaher
Assistant Examiner—Otilia Gabor
(74) Attorney, Agent, or Firm—Reed Smith LLP

(57) ABSTRACT

An arrangement for the adjustment of laser power and/or pulse length in a microscope, wherein a specimen is excited to nonlinear fluorescence, preferably two-photon fluorescence, by radiation by means of a short pulse laser, wherein the nonlinear fluorescence signal and a reflection signal and/or reference signal corresponding to the laser power are detected and the ratio of the fluorescence signal and reflection signal and/or reference signal serves as a regulating signal for adjustment.

11 Claims, 2 Drawing Sheets

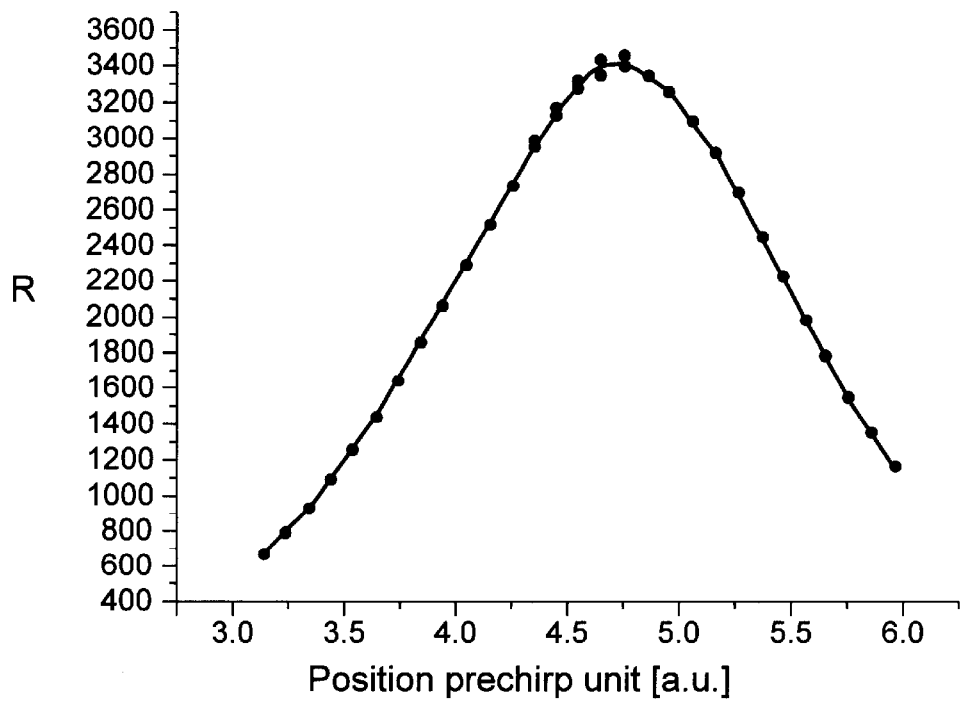
F I G. 2
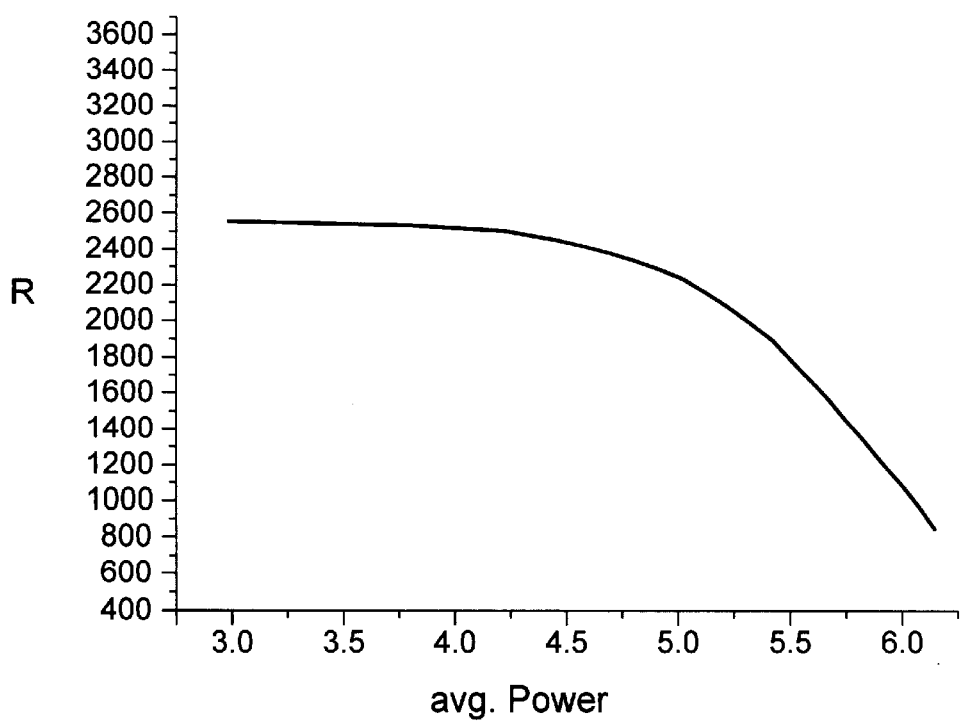
F I G. 3

ARRANGEMENT FOR THE ADJUSTMENT OF LASER POWER AND/OR PULSE LENGTH OF A SHORT PULSE LASER IN A MICROSCOPE

BACKGROUND OF THE INVENTION

For the excitation of nonlinear processes (multiphoton absorption, SHG, OBIC, time-resolved fluorescence detection, etc.) by pulsed laser in specimens, the highest possible pulse-peak powers $P_{peak}$ are needed. The pulse peak power (intensity I) is calculated as follows:

$$P_{Peak} = \frac{P_{Avg}}{\tau \cdot f \cdot A} \tag{1}$$

Accordingly, the shorter the pulse length $\tau$ in the specimen, the higher the peak power. However, short pulses have a determined spectral width $\Delta\lambda$, depending on the pulse length. The repetition rate is designated by A and the interaction surface with the specimen is designated by f. $P_{avg}$ represents the average power of the laser radiation. Due to dispersion in optical components, the pulses are broadened when traversing the optical media (including the specimen). In addition, nonlinear effects such as SPM can occur, affecting the spectrum and therefore, in turn, the pulse length. There is accordingly a need to optimize the pulse length and the average power at the location of the laser interaction with the specimen.

DESCRIPTION OF CONVENTIONAL METHODS

Short pulses of less than 1 ns can not be directly measured by electronic means because of their brevity. For this purpose, autocorrelators are used, for example; the autocorrelation function of the pulses can be determined in this way. The pulse length is subsequently determined from this autocorrelation function. However, these measuring instruments generally require a parallel beam of the laser light under examination. They are therefore unsuitable for determining the pulse length directly following a high-aperture objective. They are unsuited in principle for determining/optimizing the pulse length as a function of the depth of penetration into a specimen.

SUMMARY OF THE INVENTION

It is possible by means of the proposed method to measure the pulse length at the location of laser interaction with the specimen and to optimize the pulse peak power. The nonlinear interaction combined with a linear interaction is used for this purpose in a biological specimen.

In general, the nonlinear interaction can be described as follows:

$$S_{NL} = C \cdot P_{peak}^n = C \cdot \frac{P_{avg}^n}{(\tau \cdot f \cdot A)^n} \tag{2}$$

where C is a proportionality factor and n is the order of nonlinearity. The constant C depends on the properties of the specimen. Nonlinear specimen interactions are, e.g., two-photon absorption (n=2), the generation of the second harmonic (n=2), three-photon absorption (n=3), etc.

A linear specimen interaction is given, among others, by:

$$S_L = C_1 \cdot P_{avg} \tag{3}$$

where $C_1$ is again a proportionality factor which also depends in this case on the properties of the specimen. A linear interaction is, e.g., any reflection on the specimen, the excitation of a single-photon fluorescence, or the measurement of the average power with a power measuring instrument.

When both processes (linear and nonlinear) are measured at the same time and the ratio $$R = \frac{S_{NL}}{S_L^n} \tag{3.1}$$

is determined between the two signals, the following relationship results, for example, for a two-photon absorption:

$$(2)/(3) \quad R = \frac{S_{NL}}{S_L^n} = \frac{C}{C_1^2 \cdot f^2 \cdot A^2} \cdot \frac{1}{\tau^2} = Const. \cdot \frac{1}{\tau^2}, \tag{4}$$

where f and A are independent from the pulse length.

The proportionality constants (C, $C_1$) are normally also independent from the pulse length. In the case of two photons, the ratio R of nonlinear to linear signal is inversely proportional to the pulse length and independent from the average power. The constant (Const) depends on the specimen used and on the detection device.

The application of the invention will be explained by way of example with reference to two-photon absorption.

BRIEF DESCRIPTION OF THE DRAWINGS

In the drawings:

FIG. 2 shows the ratio R as a function of pulse length;

FIG. 3 shows the dependence of the ratio on the average power without changes to the adjustment of the prechirp unit.

DESCRIPTION OF THE PREFERRED EMBODIMENTS

For technical conversion, it is necessary to arrange two detectors D1 and D2 (FIGS. 1a and 1b) in such a way that the reflection/average power and the two-photon fluorescence are recorded simultaneously (sequentially). Subsequently, the ratio R is calculated in the computer and displayed graphically.

Figure 1A:
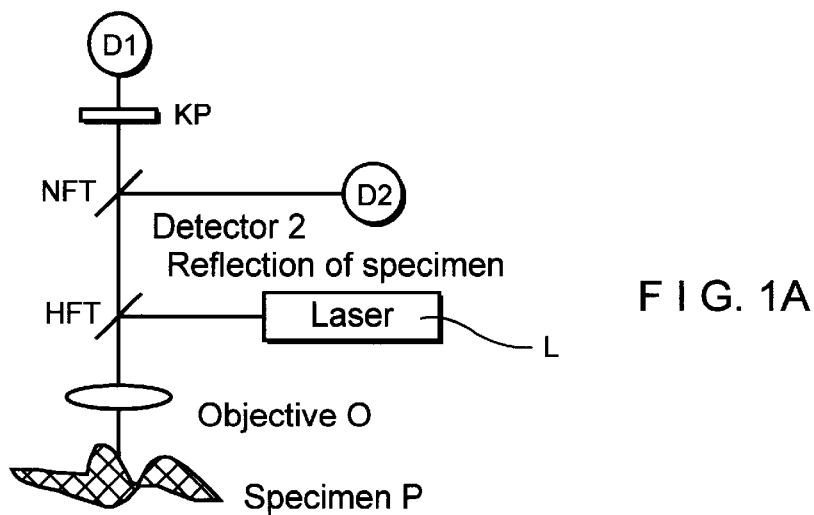
FIG. 1a shows a construction in which the reflection of the specimen P illustrated by laser L is detected by detector D2; thereafter it is separated from the fluorescent radiation.

Arrangement FIG. 1a shows a construction in which the reflection of the specimen P illuminated by a laser L is detected as a linear signal in D2 via an objective O, a main color splitter HTF and a secondary color splitter NFT. This reflection signal is separated from the fluorescence radiation by suitable dichroics NFT and arrives at D1 via a short pass filter KP.

Figure 1B:
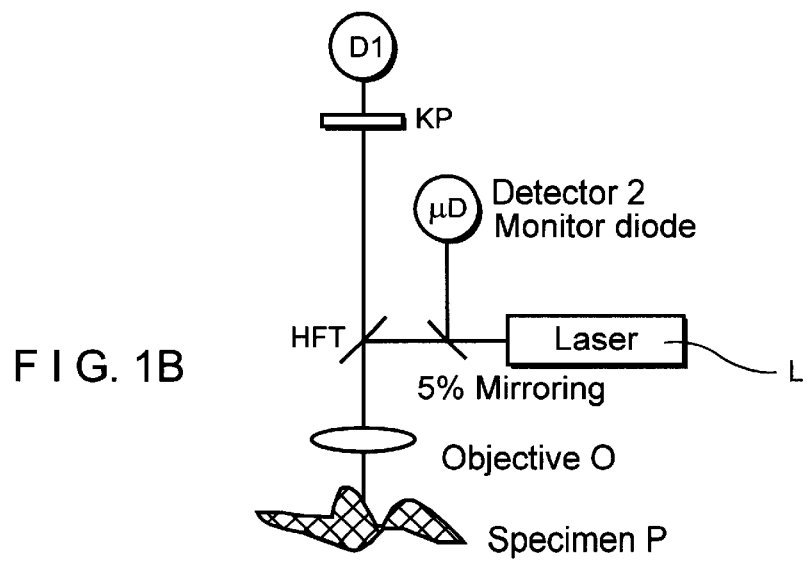
FIG. 1b shows a construction in which a monitor diode detects the average power of the radiation.

Arrangement FIG. 1b shows a construction in which a monitor diode MD, as D2, detects the average power of the laser radiation. The monitor diode is fed by a fixed mirroring of the laser light. This arrangement is preferred, since the reflection signal is independent from the reflection characteristics of the specimen in this case.

In both arrangements, a short pass filter is used as main color splitter HFT. It reflects light in the NIR wavelength range and transmits light in the VIS UV range.

FIG. 2 shows the ratio R as a function of pulse length. Illustration 2

At minimum pulse length, i.e., at maximum pulse peak power at the location of the specimen, a maximum is given in accordance with equation (4). Optimization of the pulse length can accordingly be carried out by adjusting a prechirp unit. An adjustable prechirp unit of this kind is described in DE 196 22 359A1.

It is particularly advantageous that the measurement of the characteristic quantity/ratio R in the first approximation is independent from the average power (i.e., coupling efficiency into a glass fiber, change in average output power with optimization of laser, etc.). The characteristic quantity depends exclusively on the pulse length. However, if the average power is further increased, nonlinear processes (such as self-phase modulation) can be excited in the optics used (in the fiber, in case of fiber coupling). This changes the spectral bandwidth of the (ultra-)short laser pulses and accordingly the pulse length, so that the pulse peak power is reduced. These effects, i.e., limiting the average power, are to be avoided.

The method described above can also be used to find the threshold value for the average power.

FIG. 3 shows the dependence of the ratio on the average power without changes to the adjustment of the prechirp unit (pulse length is not varied via the prechirp unit). The above-mentioned change in pulse length due to nonlinear effects in the utilized optics is expressed in the graph by a bend in the ratio which is expected to be constant in accordance with equation (4).

Figure 4:
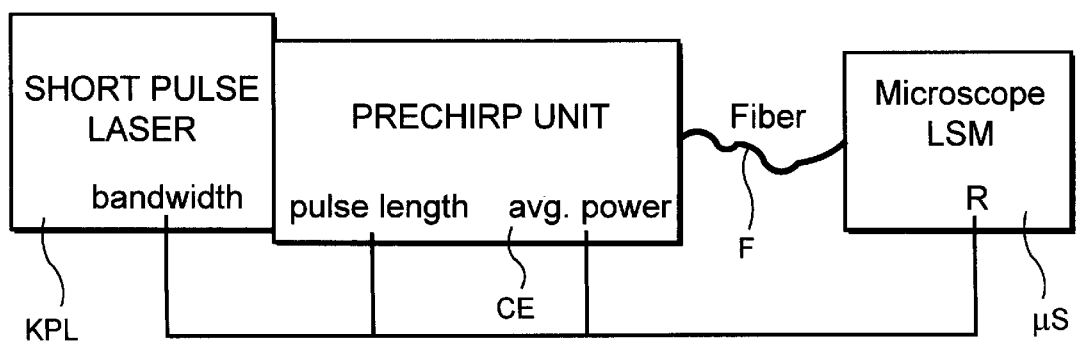
FIG. 4 shows a total arrangement comprising a short pulse laser, prechirp unit, light conducting fiber and microscope.

FIG. 4 shows a total arrangement comprising short pulse laser KPL, prechirp unit PCE, light-conducting fiber F and microscope MI, preferably a laser scanning microscope LSM.

While the foregoing description and drawings represent the preferred embodiments of the present invention, it will be obvious to those skilled in the art that various changes and modifications may be made therein without departing from the true spirit and scope of the present invention.

What is claimed is:

1. An arrangement for the adjustment of laser power and/or pulse length in a microscope, comprising:
    a short pulse laser for providing radiation for exciting a specimen to nonlinear fluorescence;
    detectors for detecting a nonlinear fluorescence signal and a reflection signal and/or reference signal corresponding to the laser power; and
    regulating signal means responsive to the ratio of the nonlinear fluorescence signal and reflection signal and/or reference signal for providing adjustment of the laser power and/or pulse length, the ratio representing the pulse length of the laser at the location of laser interaction with the specimen.

2. The arrangement according to claim 1, wherein laser light is routed to a monitor diode downstream of the laser for recording the laser power.

3. The arrangement according to claim 1 in a laser scanning microscope.

4. An arrangement for the adjustment of laser power and/or pulse length in a microscope, comprising:
    a short pulse laser for providing radiation for exciting a specimen to two-photon fluorescence;
    detectors for detecting a two-photon fluorescence signal and a reflection signal and/or reference signal corresponding to the laser power; and
    regulating signal means responsive to the ratio of the two-photon fluorescence signal and reflection signal and/or reference signal for providing adjustment of the laser power and/or pulse length, the ratio representing the pulse length of the laser at the location of laser interaction with the specimen.

5. An apparatus for adjusting laser power or pulse width in a microscope, comprising:
    a short pulse laser source that provides a laser light to excite a specimen to be observed to nonlinear fluorescence;
    a detector unit operable to detect:
        a first signal representing a nonlinear fluorescence signal responsive to the laser light; and
        a second signal representing one or both of a reflection signal of the laser light reflected from the specimen and a reference signal corresponding to the power of the laser light;
    a signal regulator operable to adjust one or both of the power and pulse width of the laser light responsive to the ratio of the first signal and the second signal, the ratio representing the pulse length of the laser light at the location of laser interaction with the specimen.

6. The apparatus according to claim 5, further comprising a pre-chirp unit coupled to and controlled by the signal regulator to adjust the power or the pulse width of the laser light.

7. The apparatus according to claim 5, wherein the detector unit includes:
    a first detector that receives light fluorescing from the specimen; and
    a second detector that receives light reflected from the specimen.

8. The apparatus according to claim 7, further comprising a short pass filter disposed in the light path between the first detector and an objective of the microscope.

9. The apparatus according to claim 5, wherein the detector unit includes:
    a first detector that receives light fluorescing from the specimen; and
    a second detector that receives at least a portion of the laser light from the light source.

10. The apparatus according to claim 9, wherein the second detector includes a monitor diode that measures the average power of the laser light.

11. The apparatus according to claim 9, wherein the laser light is transmitted to the second detector by a fixed mirroring of the laser light coming from the laser source.

* * * * *